(12) United States Patent
Herkenroth et al.

(10) Patent No.: US 9,376,367 B2
(45) Date of Patent: Jun. 28, 2016

(54) CANNABINOID CARBOXYLIC ACIDS, SALTS OF CANNABINOID CARBOXYLIC ACIDS, AND THE PRODUCTION AND USES OF SAME

(71) Applicant: The Health Concept GmbH, Frankfurt am Main (DE)

(72) Inventors: Thomas Herkenroth, Brannenburg (DE); Christian Steup, Hofheim am Taunus (DE)

(73) Assignee: The Health Concept GmbH, Frankfurt (DE)

( * ) Notice: Subject to any disclaimer, the term of this patent is extended or adjusted under 35 U.S.C. 154(b) by 45 days.

(21) Appl. No.: 14/348,459

(22) PCT Filed: Oct. 1, 2012

(86) PCT No.: PCT/EP2012/004107
§ 371 (c)(1),
(2) Date: Oct. 15, 2014

(87) PCT Pub. No.: WO2013/045115
PCT Pub. Date: Apr. 4, 2013

(65) Prior Publication Data
US 2015/0038567 A1    Feb. 5, 2015

(30) Foreign Application Priority Data
Sep. 29, 2011    (DE) .......................... 10 2011 114 528

(51) Int. Cl.
*C07C 65/19*    (2006.01)
*C07C 51/493*    (2006.01)
(Continued)

(52) U.S. Cl.
CPC ............... *C07C 65/19* (2013.01); *C07C 51/412* (2013.01); *C07C 51/42* (2013.01); *C07C 51/493* (2013.01); *C07D 311/80* (2013.01)

(58) Field of Classification Search
CPC ...... C07C 65/19; C07C 51/42; C07C 51/412; C07C 51/493; C07D 311/80
USPC .................... 514/454, 568; 562/476; 549/390
See application file for complete search history.

(56) References Cited

U.S. PATENT DOCUMENTS

| 4,025,516 A | 5/1977 | Razdan et al. |
| 5,342,971 A | 8/1994 | Herlt et al. |

FOREIGN PATENT DOCUMENTS

| DE | 10106024 A1 | 8/2002 |
| EP | 1559423 A1 | 8/2005 |

(Continued)

OTHER PUBLICATIONS

R. Mechoulam et al., Tetrahedron, 1965, 21, 1223.
(Continued)

Primary Examiner — Kristin Vajda

(74) *Attorney, Agent, or Firm* — Mintz Levin Cohn Ferris Glovsky and Popeo, P.C.

(57) ABSTRACT

The invention relates to a compound selected from the group consisting of all stereoisomers and their mixtures of the compounds of general formulas (1)-(4), in which $R^1$ is a straight-chained, branched or cyclic hydrocarbon group with up to 12 C-atoms and $X^+$ is selected from the group consisting of $H^+$, $NH_4^+$, mono, di or trivalent metal cations, $NH_4^+$, primary, secondary, tertiary or quaternary organic ammonium ions with up to 48 C-atoms, which can carry even more functional groups, hydrazinium ion ($N_2H_5^+$), hydroxylammonium ion ($NH_3OH^+$), guanidinium ion ($CN_3H_6^+$), and organic derivatives of ($N_2H_5^+$), $NH_3OH^+$, and $CN_3H_6^+$, which can carry even more functional groups, and similar. A method is also provided for producing these compounds, comprising the following steps: producing synthetic cannabinoid carboxylic acids in a chemical reaction, or extracting natural cannabinoid carboxylic acids from plant material or cell cultures of *Cannabis sativa*, and adding a suitable inorganic base, a suitable organic base and/or a suitable inorganic or organic salt in a suitable solvent, to the cannabinoid carboxylic acids or cannabinoid carboxylic acid-rich extracts produced in this manner.

(1)

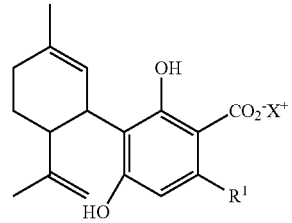

(2)

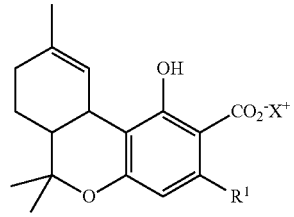

(3)

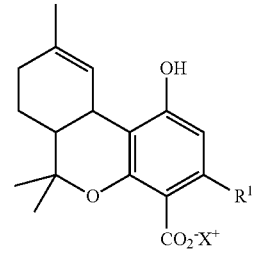

(4)

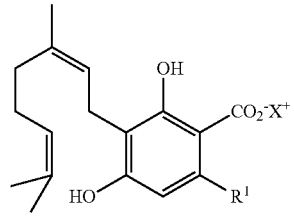

30 Claims, No Drawings

(51) Int. Cl.
*C07C 51/41* (2006.01)
*C07D 311/80* (2006.01)
*C07C 51/42* (2006.01)

(56) References Cited

FOREIGN PATENT DOCUMENTS

| EP | 2314580 A1 | 4/2011 |
|----|------------|--------|
| WO | WO-9414790 A1 | 7/1994 |
| WO | WO-0025127 A1 | 5/2000 |
| WO | WO-03064407 A2 | 8/2003 |

OTHER PUBLICATIONS

F. Korte et al., Angew. Chem. Internatl. Ed. 1965, 4, 872.
R. Mechoulam et al., Tetrahedron Letters, 1969, 2339.
R. Mechoulam et al., Chem. Communications, 1969, 343-344.
Crombie et al., J. Chem. Research, 1977, 1301-1345.
International Search Report and Written Opinion, Jan. 23, 2013, International Patent Application PCT/EP2012/004107.
International Preliminary Report on Patentability, Apr. 1, 2014, International Patent Application PCT/EP2012/004107.

CANNABINOID CARBOXYLIC ACIDS, SALTS OF CANNABINOID CARBOXYLIC ACIDS, AND THE PRODUCTION AND USES OF SAME

CROSS REFERENCE TO RELATED APPLICATIONS

The present application is a 35 U.S.C. §371 national stage entry of PCT/EP2012/004107, which has an international filing date of Oct. 1, 2012, and claims priority to German Patent Application No. 102011114528.5, filed on Sep. 29, 2011, contents of each of which are incorporated herein by reference in its entireties.

TECHNICAL FIELD

The invention relates in general to cannabinoid carboxylic acids. In particular the invention relates to salts of cannabinoid carboxylic acids, processes for the production thereof and uses thereof.

PRIOR ART

Cannabinoids occur in the hemp plant *Cannabis sativa* in the form of their carboxyl derivatives, the cannabinoid carboxylic acids, from which the so-called "neutral cannabinoids" are derived by decarboxylation, i.e. elimination of $CO_2$. Thus for example cannabidiol (CBD-(I)) is formed by decarboxylation of cannabidiolic acid (CBDA-(II)).

(I)

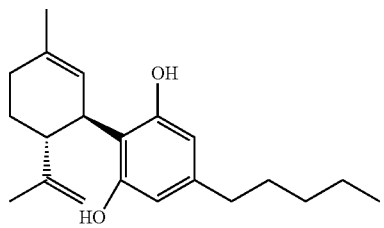

(−)-CBD 2-((1R,6R)-3-methyl-6-(prop-1-en-2-yl)cyclohex-2-enyl)-5-pentylbenzene-1,3-diol (II)

Cannabidiolic Acid (CBDA)

2,4-dihydroxy-3-((1R,6R)-3-methyl-6-(prop-1-en-2-yl)-cyclohex-2-enyl)-6-pentylbenzoic acid $\Delta^9$-tetrahydrocannabinol ($\Delta^9$-THC-, Dronabinol—(III)) is formed by decarboxylation from the positionally isomeric $\Delta^9$-tetrahydrocannabinol carboxylic acids, $\Delta^9$-tetrahydrocannabinolic acid A (THCA-A—(IV)) and $\Delta^9$-tetrahydrocannabinolic acid B (THCA-B—(V)).

(III)

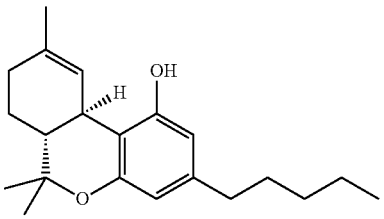

(−)-$\Delta^9$-THC (6aR,10aR)-6,6,9-trimethyl-3-pentyl-6a,7,8,10a-tetrahydro-6H-benzo[c]chromen-1-ol (IV)

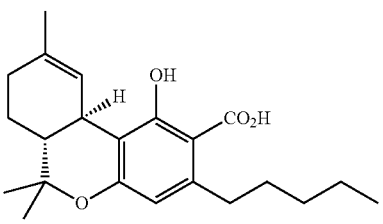

$\Delta^9$-Tetrahydrocannibinolic Acid A (THCA-A)

(6aR,10aR)-1-hydroxy-6,6,9-trimethyl-3-pentyl-6a,7,8,10a-tetrahydro-6H-benzo[c]chromen-2-carboxylic acid (V)

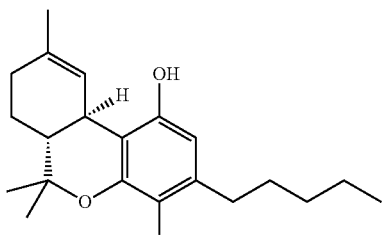

$\Delta^9$-Tetrahydrocannibinolic Acid B (THCA-B)

(6aR,10aR)-1-hydroxy-6,6,9-trimethyl-3-pentyl-6a,7,8,10a-tetrahydro-6H-benzo[c]chromen-4-carboxylic acid)

Cannabigerol (VI) is formed in this manner from cannabigerolic acid (CBGA—(VII)).

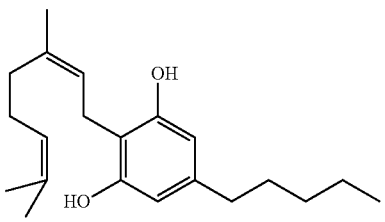

Cannabigerol (CBG)

(Z)-2-(3,7-dimethylocta-2,6-dienyl)-5-pentylbenzene-1,3-diol (VI)

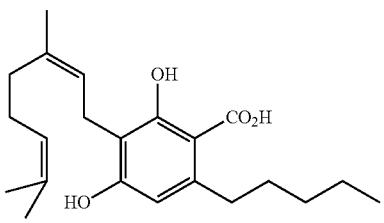

Cannabigerolic Acid (CBGA)

(Z)-3-(3,7-dimethylocta-2,6-dienyl)-2,4-dihydroxy-6-pentylbenzoic acid (VII)

The same also applies analogously for the naturally occurring trace cannabinoids such as for example $\Delta^8$-tetrahydrocannabinol, cannabicyclol, cannabicitran, cannabielsoin or homologs of said cannabinoids. Also, in the case of a closed pyran ring as with $\Delta^9$-THC (III), two positionally isomeric carboxylic acids A and B are in each case possible. Both forms occur in nature (e.g. see R. Mechoulam et al., Tetrahedron, 1965, 21, 1223; F. Korte et al., Angew. Chem. Internatl. Ed., 1965, 4, 872 and R. Mechoulam et al., Tetrahedron Letters, 1969, 2339).

Previously, compounds such as dronabinol (III) and homologs thereof had to be purified by laborious processes such as preparative chromatography. Thus U.S. Pat. No. 4,025,516 discloses a process for the production of dronabinol by condensation of (+)-p-mentha-2,8-dien-1-ol with olivetol in the presence of $BF_3$ etherate. The synthesis of dronabinol from cannabidiolic acid esters in the presence of Lewis acids followed by hydrolysis is known from U.S. Pat. No. 5,342,971. The production of dronabinol from tetrahydrocannabinol-rich *Cannabis* followed by distillation and/or chromatography is described in the international patent application WO 00/25127. Finally, DE 101 06 024 B4 discloses a process for the production of dronabinol wherein a) cannabidiol and/or cannabi-diolic acid is isolated from plant materials, b) the cannabidiolic acid obtained by decarboxylation if necessary is cyclized to dronabinol in an organic or nonpolar solvent in the presence of Lewis catalysts, c) this is isolated by a chromatographic process and d) the residue obtained from the eluate after distilling off the solvent is purified by vacuum distillation.

The production of crystallizable precursors such as the ester (e.g. of the 3,5-dinitrobenzoyl ester), crystallization thereof and the subsequent saponification are relatively laborious and moreover associated with the risk of creating further impurities.

The reaction which results in the formation of the neutral cannabinoids from the aforesaid cannabinoid carboxylic acids as a rule proceeds slowly at room temperature, but can be accelerated by heating and/or addition of catalysts so that the $CO_2$ loss proceeds within a few minutes or practically immediately. This reaction can be controlled so that it proceeds practically quantitatively and without the formation of further side products.

From the aforesaid, it follows that pure cannabinoid carboxylic acids are practically ideal precursors for obtaining pure neutral cannabinoids therefrom. Hence it would be a significant advance for the production of pure cannabinoids to be able to provide a process which makes it possible to obtain and purify cannabinoid carboxylic acids economically.

Hence the invention is based on the objective of providing a process for the production of salts which are as pure as possible, preferably crystalline salts of natural or synthetic cannabinoid carboxylic acids, from which pure neutral cannabinoids can be obtained in a simple manner.

A further objective consists in providing a process which can be performed with relatively little expenditure and is less susceptible to the formation of impurities.

DISCLOSURE OF THE INVENTION

The present invention solves this problem by providing a process for the production of crystalline and soluble salts of cannabinoid carboxylic acids by production of synthetic cannabinoid carboxylic acids in a chemical reaction or extraction of natural cannabinoid carboxylic acids from plant materials or cell cultures of *Cannabis sativa* and subsequent treatment with a suitable organic base, inorganic base and/or a suitable inorganic or organic salt in a suitable solvent.

The present invention solves this problem by providing a process for the production of amorphous and crystalline salts, in particular pure, preferably crystalline salts of cannabinoid carboxylic acids by production of synthetic cannabinoid carboxylic acids in a chemical reaction or extraction of natural cannabinoid carboxylic acids from plant materials or cell cultures of *Cannabis sativa* and subsequent treatment with a suitable organic base, inorganic base and/or a suitable inorganic or organic salt in a suitable solvent. Here, pure is understood to relate to substance mixtures with a salt content of >90 wt. %.

The present invention comprises the production of natural or synthetic cannabinoid carboxylic acids and salts thereof (1) to (4), including all stereoisomers and mixtures thereof, in particular the production for the first time of crystalline salts of cannabinoid carboxylic acids, purification thereof by recrystallization and the obtention of pure neutral cannabinoids therefrom.

Further, processes are disclosed by means whereof amorphous or crystalline salts can be obtained from cannabinoid carboxylic acids or amorphous or dissolved salts of cannabinoid carboxylic acids can be converted into crystalline salts and by means whereof pure neutral cannabinoids can be produced from pure cannabinoid carboxylic acids or salts thereof.

(1)
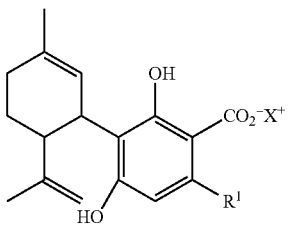

(2)
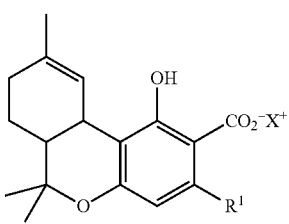

(3)
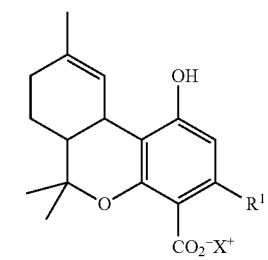

(4)
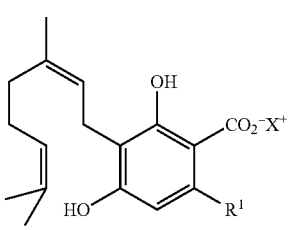

Therein, $R^1$ is a straight-chain, branched or cyclic hydrocarbon residue with one C atom to 12 C atoms.

$X^+$ is preferably selected from the group consisting of $NH_4^+$, mono-, di- or trivalent metal ions, and primary, secondary, tertiary or quaternary organic ammonium ions with up to 48 C atoms, which may bear still further functional groups.

Examples of multivalent ammonium ions are N,N-dicyclohexylamine-$H^+$ and N,N-dicyclohexyl-N-ethylamine-$H^+$. $X^+$ can also be the hydrogenium cation of a pharmaceutical active substance with at least one basic nitrogen atom, such as for example morphine, methadone (or an enantiomer thereof) or hydromorphone.

The production of pure, preferably crystalline salts of cannabinoid carboxylic acids comprises two steps: in a first step, synthetic cannabinoid carboxylic acids are produced in a chemical reaction or natural cannabinoid carboxylic acids extracted from plant material or cell cultures of *Cannabis sativa*.

In a second step, the cannabinoid carboxylic acids or cannabinoid carboxylic acid-rich extracts thus produced are treated in a suitable solvent with a suitable organic base, a suitable inorganic base and/or a suitable inorganic or organic salt, so that the poorly soluble salts of the cannabinoid carboxylic acids precipitate out. These can be separated for example by filtration and if necessary purified by recrystallization.

In a further step, pure cannabinoids can be produced from the pure, preferably crystalline salts thus produced.

This can be effected by displacement of the cannabinoid carboxylic acids by means of another acid, extraction of the pure cannabinoid carboxylic acids and subsequent thermal or catalytic decomposition, or by decomposition of the salts of cannabinoid carboxylic acids with primary, secondary or tertiary amines (but not quaternary ammonium salts), which can also take place with thermal or catalytic assistance.

The invention further comprises cannabinoid carboxylic acid-containing liquids and cannabinoid carboxylic acid salt-containing liquids for medicinal vaporizers.

Such liquids are preferred compared to the oral dronabinol preparations which have the disadvantage of low and markedly varying bioavailability, which moreover also display low stability to oxidation.

1. Production and Isolation of Cannabinoid Carboxylic Acids 1.1 Synthetic Production of Cannabinoid Carboxylic Acids Method A:

Cannabinoid carboxylic acids can be produced synthetically by carboxylation from neutral cannabinoids by processes known from the literature. On this, see R. Mechoulam et al.: Chem. Communications, 1969, 343-344. Both natural and synthetic cannabinoids can be used as starting materials.

Method B:

Synthetic cannabinoid carboxylic acids can be constructed by acid-catalyzed terpenylation of alkylresorcyl esters (6-alkyl-2,4-dihydroxybenzoates) (5) and subsequent saponification of the esters as described in Crombie et al.: J. Chem. Research pp. 1301-1345 (1977). In this terpenylation, the use of the optically active compounds (6a) and (7a) respectively leads to the natural stereoisomers of the desired cannabinoid carboxylic acids and cannabinoids.

(5)
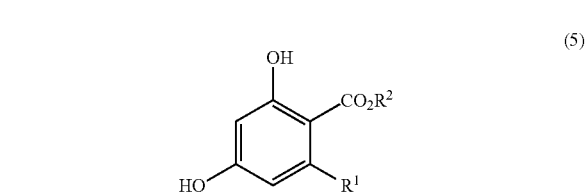

Here, $R^1$ is as defined above. $R^2$ is H or a straight-chain or branched alkyl with up to 16 C atoms, which may bear further substituents such as phenyl, hydroxy, methoxy, ethoxy, halogen or nitrile.

In the terpenylation, compounds of the type (5) react with terpenes such as p-menthadienol (6), verbenol (7) and geraniol (8).

(6)
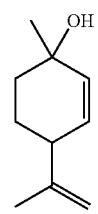

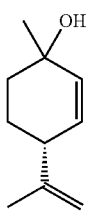

(6a)=(4R)-1-methyl-4-(prop-1-en-2-yl)cyclohex-2-enol

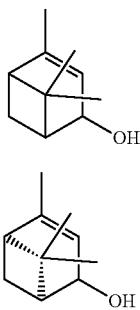

(7a)=(1R,5R)-4,6,6-trimethylbicyclo[3.1.1]hept-3-en-2-ol

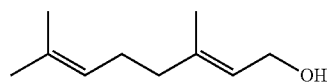

3,7-dimethylocta-2,6-dien-1-ol

Both Brönstedt acids and Lewis acids are acids suitable for the terpenylation. Examples of suitable Brönstedt acids are: perchloric acid, hydrohalic acids (HF, HCl, HBr and HI), sulfuric acid, hydrogen sulfates, phosphoric acid and acid salts thereof, pyro- and polyphosphoric acids, organic carboxylic and sulfonic acids with one to 30 carbon atoms and one or more acidic groups, and acidic groups bound onto polymeric supports such as for example acidic ion exchangers and mixtures of said acids. Formic acid, oxalic acid, trifluoroacetic acid and p-toluenesulfonic acid may be mentioned by name.

The invention includes by reference the entirety of the disclosure content of the European patent application EP 2 314 580 (Application No. 10 004 422.1-2117), at least regarding the procedure described therein for the acid-catalyzed terpenylation for the production of the precursors of the salts according to the invention.

Examples of suitable Lewis acids are the cations of alkaline earth metals, earth metals and transition metals: the halogen compounds and other trivalent compounds of elements of the third main group such as boron trifluoride and other boron halogen compounds and complexes thereof, aluminum halides such as anhydrous aluminum chloride, salts and halogen compounds of transition metals such as titanium tetrachloride, zinc chloride and zinc trifluoromethanesulfonate, halogen compounds of elements of the fourth and fifth and sixth main group such as for example tin tetrachloride, phosphorus trichloride, phosphorus pentachloride, phosphorus oxychloride, antimony pentafluoride, thionyl chloride and sulfuryl chloride, alone or mixed with other Lewis or Brönstedt acids, and positive centers bound onto polymeric frameworks such as montmorillonite.

Further suitable reagents for performing the condensation are the acetals of N,N-dimethylformamide such as for example N,N-dimethylformamide dineopentyl acetal and other water-abstracting reagents, for example those which are used for the formation of amides and peptides such as for example PPAA (T3P=propanephosphonic acid anhydride).

These reagents can be added as such to the reaction mixture or be applied onto a support material such as for example aluminum oxide.

Suitable solvents for performing the terpenylation step are water, solvents immiscible with water or miscible with water such as for example hydrocarbons with up to 30 carbon atoms, halogenated hydrocarbons with up to 20 C atoms such as for example dichloromethane or chloroform, ethers such as for example 2-methyltetra-hydrofuran, alcohols, carboxylic acids with up to 16 C atoms, amides with up to 20 C atoms, esters with up to 60 C atoms, carbon dioxide, sulfur dioxide, water, water with a phase transfer catalyst, the acidic catalysts themselves, and mixtures of said solvents with one another.

To perform the process, an as a rule equimolar mixture of 6-alkyl-2,4-dihydroxybenzoic acids (5) and the relevant terpene in one of said solvents is treated with a catalytic to ca. equimolar quantity of acid and stirred at a temperature between minus 40° C. and plus 120° C. until the reaction has reached the desired degree (tests by thin layer chromatography or HPLC).

Next the acid is neutralized with an aqueous base such as aqueous sodium hydrogen carbonate, and the organic layer is separated and evaporated. Cannabinoid carboxylic acid esters are thus obtained, which as described by Crombie et al. can be saponified to the corresponding cannabinoid carboxylic acids.

Method C:

The cannabinoid carboxylic acids (II), (IV), (V) and (VII) and homologs thereof can also be constructed directly from 6-alkyl-2,4-dihydroxybenzoic acids (5: $R^2$=H) and the corresponding terpenes. Here the same reagents and solvents are used as with the esters of the 6-alkyl-2,4-dihydroxybenzoic acids.

By construction from non-esterified 6-alkyl-2,4-dihydroxybenzoic acids, the subsequent saponification step is avoided.

1.2 Extraction of Cannabinoid Carboxylic Acids from Natural Plant Material from *Cannabis Sativa* or from Cell Cultures The aboveground growing parts of *Cannabis sativa* (hemp) and cell cultures of this species contain the cannabinoid carboxylic acids (II), (IV), (V) and (VII), and further cannabinoid carboxylic acids and low homologs thereof in usable quantities. Advantageously, a resin-rich extract of plant parts, such as can for example be obtained by the "Ice-o-later" process or by sieving out the resin glands, can be used for further concentration of the cannabinoid carboxylic acids.

By extraction with a suitable solvent, a cannabinoid carboxylic acid-rich extract wherein, depending on the crop variety of *Cannabis sativa*, one of said cannabinoid carboxylic acids predominates can be obtained therefrom.

For this, plant parts dried as necessary or cell cultures are contacted with a suitable solvent and thus respectively the cannabinoid carboxylic acids mainly stored on the outside of the cell are "washed" off or the cell cultures extracted.

Advantageously, the desired cannabinoid carboxylic acids are concentrated in the solvent by using already cannabinoid carboxylic acids-containing extract for the extraction of further plant materials.

Advantageously, the countercurrent process is used for this, i.e. the cannabinoid carboxylic acid-containing extract is again used to extract fresh (not yet extracted) plant material and fresh solvent first used for already extracted hemp.

By cautious evaporation at low temperatures, preferably below 60° C., the cannabinoid carboxylic acids can thus be concentrated in the crude extract.

If necessary, this is performed under reduced pressure in order to lower the boiling point of the solvent.

i) Suitable solvents immiscible with water:

Hydrocarbons with up to 30 C atoms, also liquefied hydrocarbons gaseous in the normal state such as propane and/or butane, petroleum distillates such as petroleum ether ligroin, kerosene, naphtha, halogenated hydrocarbons with up to 12 C atoms, carbon disulfide, esters and ethers with up to 16 C atoms, alcohols, ketones and nitriles with at least 4 and up to 12 C atoms, and mixtures of said solvents.

ii) Suitable solvents miscible with water

Water with basic additives, such as for example ammonia, alkylamines, hydroxylamine, hydrazine, metal hydroxides, metal carbonates or metal hydrogen carbonates, water with detergents, lower alcohols with up to 4 C atoms, acetonitrile, propionitrile, acetone, and mixtures of said solvents.

iii) Also carbon dioxide and liquefied sulfur dioxide, liquefied ammonia and liquefied alkylamines, also with additions of the solvents mentioned in i) and ii).

From water immiscible solvents, the cannabinoid carboxylic acids can also be separated from the neutral components by washing with aqueous alkali. For this, an extract prepared with one of the solvents named in i) is contacted with an aqueous ammonia or alkali solution such as for example 1% aqueous KOH by stirring or shaking. The phases are then allowed to separate and the aqueous phase which now contains the pre-purified (largely freed from neutral components) cannabinoid carboxylic acids in the form of their soluble salts is separated.

By cautious acidification (neutralization) with an acid, the extracted cannabinoid carboxylic acids can be precipitated from this and if necessary extracted with one of the solvents named in i).

Example 100 g of dried (or ca. 300 g of fresh) flowering tops and leaves of Cannabis sativa (THC type of the "white widow" variety) are extracted with 1 l of petroleum ether at <40° C. Next the undissolved plant components are removed by filtration. This first extract is stirred with 0.5 l of aqueous 0.1 molar potassium hydroxide solution, to which 5 g of sodium sulfite can be added to protect against oxidation. This second, aqueous extract is separated and treated with a solution of 5 g of citric acid in 50 ml water, whereupon the cannabinoid carboxylic acids precipitate as an oil. By addition of 200 ml petroleum ether and stirring, a third extract is now prepared. Removal of the organic phase and evaporation under reduced pressure at 40° C. yields 15.7 g of an oily residue, which 80% consists of a mixture of the $\Delta^9$-THC acids A and B.

From the extracts obtained with the solvents named in ii) and iii), crude cannabinoid carboxylic acids can be obtained by evaporation, preferably below 60° C.

From extracts obtained with water with basic additives, the cannabinoid carboxylic acids can be obtained by cautious acidification (neutralization) and extracted with one of the solvents named in i) if necessary.

Cannabinoid carboxylic acids from hemp extracts can also be separated from non-acidic components by means of basic ion exchangers.

2. Crystalline Salts of Cannabinoid Carboxylic Acids 2.1 Precipitation of Crystalline Salts with Suitable Bases If cannabinoid carboxylic acids or cannabinoid carboxylic acid-containing extracts in a suitable solvent are reacted with a suitable base, crystalline salts are formed, which can be separated.

Suitable solvents are alcohols, esters, ethers, ketones, hydrocarbons, halogenated hydrocarbons and nitriles with up to 20 C atoms.

Suitable bases for the formation of crystalline salts are primary, secondary and tertiary organic amines with up to 48 C atoms such as for example dicyclohexylamine, ammonia, alkoxides, hydroxides, carbonates, hydrogen carbonates, carboxylates and other basic salts of elements of the first, second and third main group and of tin, lead and bismuth, and the alkoxides, hydroxides, carbonates, hydrogen carbonates, carboxylates and other basic salts of transition elements such as for example silver ($Ag^+$). Inorganic salts may be complexed (e.g. silver hydroxide as silver diammine complex) in order to increase the solubility. Further suitable organic bases are pharmaceutical active substances with at least one basic nitrogen atom in the molecule, such as for example morphine, hydromorphone (Palladon®), buprenorphine, etc.

Procedure:

A quantity of base equivalent to the expected quantity of desired cannabinoid carboxylic acids is added with stirring to the solution of the cannabinoid carboxylic acids in a suitable solvent. Preferably ca. 2% to 20% solutions of cannabinoid carboxylic acids are used here. This is allowed to crystallize overnight and the crystallization is if necessary completed by cooling to ca. −10° C. Next, the precipitated crystalline slurry is suction filtered/centrifuged down and rinsed with a small quantity of the same solvent as was used for the precipitation. The salt is then allowed to dry at <40° C. It can be purified by suspension in one of the aforesaid solvents, digestion and suction filtration of the undissolved matter. It can also be recrystallized from a suitable solvent, preferably a lower alcohol, nitrile, ketone, ester or ether with up to 4 C atoms.

Example 15.7 g of a ca. 80% mixture of $\Delta^9$-THC acids A and B are dissolved in 150 ml isopropanol with stirring and 8.0 g of dicyclohexylamine are added with stirring. 24 hrs stirring at 0° C. produces a thick white precipitate of the dicyclohexylamine salts of the cannabinoid carboxylic acids. After suction filtration, washing with 50 ml cold isopropanol and drying, 18.7 g of dicyclohexylamine salt of the $\Delta^9$-THC acids with a content of 91% are obtained.

Precipitation of the Dicyclohexylamine Salt of CDBA from an Isopropanolic Industrial Hemp Extract Example 2 kg of flowering tops of industrial hemp (e.g. of the variety Fedora 19, but others are also possible) dried at below 30° C. are extracted portionwise with cold (<15° C.) isopropanol by the countercurrent process. The extract obtained is concentrated under reduced pressure at max. 40° C. to a volume of ca. 400 ml. This concentrate is treated 12 g of dicyclohexylamine and stirred for 24 hrs at 0° C. The dicyclohexylamine salt of cannabidiolic acid crystallizes, and is suction filtered off. Rinsing with 80 ml of ice-cold isopropanol and drying under vacuum gives 22.4 g of cream-colored salt.

2.2 Precipitation of Salts by Addition of a Suitable Cation to a Solution of Cannabinoid Carboxylic Acids To a solution of cannabinoid carboxylic acids in a suitable solvent is added an equivalent quantity of a base which in the solvent used forms amorphous or soluble salts with the corresponding cannabinoid carboxylic acids, such as for example ammonia. Next, the solution of a suitable primary, secondary, tertiary or quaternary ammonium salt or a metal salt of the first, second, third, fourth or fifth main group, a lanthanide metal or a transition metal such as for example silver in a suitable solvent is added to the solution of the cannabinoid carboxylic acid salts. Suitable solvents are those named in 2.1.

Suitable primary, secondary, tertiary or quaternary ammonium salts are organic ammonium salts with up to 48 C atoms, which may bear further functional groups.

The solvent and the ammonium salt or metal salt are selected such that the relevant cation forms a poorly soluble precipitate with the anions of the cannabinoid carboxylic acids in the relevant solvent.

The corresponding poorly soluble cannabinoid carboxylic acids salt precipitates, and is isolated by suction filtration or centrifugation.

2.3 Recrystallization of Cannabinoid Carboxylic Acid Salts

Since the cannabinoid carboxylic acid salts are more stable to decarboxylation than the free acids, the salts thus precipitated can be purified by recrystallization. The same solvents can be used for the recrystallization as for the precipitation. The crystallization is preferably from a lower alcohol, ketone, nitrile, ester or ether with up to 8 C atoms. The addition of a catalytic quantity of complexing agents for metal cations, such as for example EDTA sodium or a crown ether, can increase the stability of the cannabinoid carboxylic acid salts during the recrystallization procedure. This purification process has the advantage that it is considerably simpler to perform compared to the processes conventionally used with cannibinoids, such as chromatography.

Example 18.7 g of dicyclohexylamine salt of $\Delta^9$-THCA A and B with a content of 91% $\Delta^9$-THC acids in the cannabinoid content are dissolved with stirring in 150 ml of boiling absolute ethanol, and cooled immediately after dissolution has occurred. Stir overnight at 0° C. to crystallize out. Suction filter the white precipitate formed and wash with 50 ml cold absolute ethanol. Yield: 15.5 g of pure white salt with a content of >97% of $\Delta^9$-THC acids (A and B) in the cannabinoid content.

This product is of sufficient purity to yield pharmaceutically usable dronabinol as per DAC 2003 after decarboxylation.

A further use of the cannabinoid carboxylic acid salts thus produced is as stable additives to dermatological products. For this, salts of cannabinoid carboxylic acids which have been formed with bases toxicologically harmless or therapeutically active in man or animals are preferably used. These salts need not be crystalline, but can also be used in amorphous form and be added to the dermatological products. They are characterized by increased stability (shelf life) compared to free cannabinoid carboxylic acids. A further stabilization can be achieved by addition of metal complexing agents such as for example EDTA sodium, which complex metal ions which catalyze the decarboxylation of cannabinoid carboxylic acid salts.

3. Obtention of Pure Cannabinoids from Salts of Cannabinoid Carboxylic Acids 3.1 Production of Pure Cannabinoids from Cannabinoid Carboxylic Acid Salts by Displacement of the Free Cannabinoid Carboxylic Acids By addition of an acid to cannabinoid carboxylic acid salts, the carboxylate anions are reprotonated and the free lipophilic acids can be extracted with a suitable solvent. Suitable solvents for this are those named in 1.2.i).

Suitable acids are water-soluble Brönstedt acids with a $pK_a$ below 7, and carbonic acid (generated for example by passing $CO_2$ into water).

Preferably, readily volatile solvents are used which have a boiling point below 160° C. at normal pressure. After removal of the solvent by distillation, preferably at low temperature such as <60° C., preferably <40° C., the free cannabinoid carboxylic acids remain as a residue.

Example 15.0 g of recrystallized dicyclohexylamine salt of the tetrahydrocannabinolic acids A and B are suspended in 200 ml water and overlayered with 200 ml petroleum ether. 3.0 g of citric acid are now added and the mixture stirred until the cannabinoid carboxylic acid salt has completely dissolved. The aqueous phase, which now contains the citrate of dicyclohexylamine, is separated and discarded. The petroleum ether phase, which now contains the free $\Delta^9$-tetrahydrocannabinolic acids, is successively washed once with 50 ml of 1% citric acid and three times with 50 ml portions of water. After evaporation of the petroleum ether phase on the waterbath at 40° C. under reduced pressure, 9.8 g of amorphous residue of the two positionally isomeric $\Delta^9$-tetrahydrocannabinolic acids remain.

3.1.1 Cannabinoids by Thermal Decomposition (Decarboxylation) of Cannabinoid Carboxylic Acids By heating to a temperature >60° C., preferably over 100° C., the free cannabinoid carboxylic acids are decarboxylated, i.e. they are converted into the corresponding neutral cannabinoids by loss of carbon dioxide. This is preferably performed in vacuo or under an inert gas atmosphere in order to prevent oxidation of the cannabinoids formed. If this is performed under a sufficient vacuum, preferably below 0.3 mbar, the product can immediately be distilled at a temperature of preferably over 140° C. If the heating is performed in a current of gas, the vapors of the neutral cannabinoids produced can be administered medicinally.

Example 9.8 g of $\Delta^9$-tetrahydrocannabinolic acids (A and B) with a purity of 97.8% determined by HPLC are heated at 160° C. for 30 mins in a current of nitrogen. After carbon dioxide evolution has ceased, 8.4 g of dronabinol with a purity of 97.6% (HPLC) remain.

3.1.2 Cannabinoids by Catalytic Decomposition (Decarboxylation) of Cannabinoid Carboxylic Acids Catalysts can accelerate the decarboxylation of cannabinoid carboxylic acids so that this practically instantaneously proceeds quantitatively. This was observed by the rapid onset of bubble formation ($CO_2$) in free cannabinoid carboxylic acids on metal surfaces such as steel. Suitable catalysts are elements of the transition metals in finely divided form or with activated surfaces and ions of transition metals. Conversely, the deactivation of surfaces or the addition of complexing agents can be used in order to stabilize cannabinoid carboxylic acids and salts thereof.

Example

In a medicinal inhaler (e.g. "Vulcano"), 0.05 ml of a 5% ethanolic solution of pure $\Delta^9$-tetrahydrocannibinolic acids (A and B) is applied onto the metal wire gauze of the vaporizer part. A current of hot gas at 230° C. is then allowed to pass through the vaporizer part for 60 secs. Finely divided $\Delta^9$-tetrahydrocannibinol of pharmaceutical purity for inhalation for medicinal use collects in the receiver (collector part).

3.2 Cannabinoids by Decomposition of Cannabinoid Carboxylic Acid Salts

In the cold and at room temperature, the salts of cannabinoid carboxylic acids are stable substances, storable undecomposed for years. Moreover, crystalline salts of cannabinoid carboxylic acid can be particularly easily and effectively purified by recrystallization. These properties can be exploited in order to use them as quantitative and qualitative standards in analytical chemistry.

3.2.1 Thermal Decomposition of Cannabinoid Carboxylic Acid Salts

The salts of cannabinoid carboxylic acids with primary, secondary and tertiary amines have a mobile hydrogenium ion ($H^+$) in the cation, which at elevated temperature is in perceptible equilibrium with the carboxylate anion of the cannabinoid carboxylic acids component. In the reprotonated state, the cannabinoid carboxylic acids are readily accessible to decarboxylation to the corresponding neutral cannibinoids. Thus, if cannabinoid carboxylic acid salts of ammonia, primary, secondary and tertiary amines, hydrazine, hydroxylamine, guanidine and organic derivatives thereof are strongly heated, carbon dioxide is readily evolved and mixtures of the free amines and the neutral cannabinoids are formed. At elevated temperature, particularly in vacuo or in a current of gas, these are present in vapor form and can for example be used for inhalation.

A further use consists in the use of the salts of cannabinoid carboxylic acids, stable in the cold and at room temperature, as reference substances and standards for gas chromatography. This is particularly advantageous in cases where the cannabinoids formed are unstable, oxidation-sensitive substances, such as for example in the case of $\Delta^9$-tetrahydrocannabinol.

In these cases, a solution of a stable salt such as for example the dicyclohexylamine salt of $\Delta^9$-tetrahydro-cannabinolic acid A or B is injected into the injector of the gas chromatograph. Because of the high temperature of the injection block (as a rule >230° C.), the salt immediately decomposes quantitatively into the neutral cannabinoid (in the case of the example $\Delta^9$-tetra-hydrocannabinol), the amine and $CO_2$. The amine (in the case of the example dicyclohexylamine) is separated by the chromatography system as a separate peak and does not affect the quantification of the cannabinoid.

In a medicinal inhaler, the decomposition of cannabinoid carboxylic acid salts as substance or solution with pharmaceutically active amines such as analgesics or local anesthetics can be used for a combination therapy, or to mask the irritation cough effect of cannabinoids such as dronabinol. The thermal decomposition of a salt of cannabinoid carboxylic acids with vaporizable pharmacologically active amines has the effect that both the neutral cannabinoid and also the amine component are nebulized and are available in the form of an aerosol for inhalation. The finely divided nature of the aerosol droplets and the parenteral administration result in significantly increased bioavailability compared to oral dosage forms.

In preparative chemistry, the separation of basic substances such as amines from neutral cannabinoids is no problem (see under 3.1), so that the salts of cannabinoid carboxylic acids with primary, secondary and tertiary amines are also outstandingly suitable for use for the preparation of pure cannabinoids.

3.2.2 Catalytically Assisted Decomposition of Cannabinoid Carboxylic Acid Salts

In the decarboxylative decomposition of cannabinoid carboxylic acid salts, the same substances named in 3.1.2 also act catalytically as with the free cannabinoid carboxylic acids. For more rapid conversion to cannabinoids, the salt is moistened with a dilute (e.g. 0.1%) solution of a transition metal such as for example iron-[III] chloride or silver nitrate. The salt is then dried. Alternatively, the salt is thoroughly contacted with a small quantity of transition metals such as for example 0.1 wt. % steel powder or steel wire or 0.01% silver powder. Now the salt is heated either dry or together with an inert heat transfer agent, such as for example a high-boiling hydrocarbon. After the salt has been decarboxylated, e.g. by heating under inert gas for 30 mins at 180° C., the procedure described in 3.1 is followed in order to separate the cannabinoid from the amine.

It is clear to those skilled in the art that the processes described in this application are applicable not only for the compounds explicitly mentioned, but for all homologs, stereoisomers thereof and for mixtures thereof (e.g. racemates).

The invention claimed is:
1. A compound chosen from formulae (1)-(4)

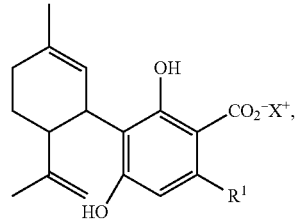

(1)

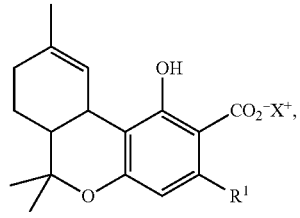

(2)

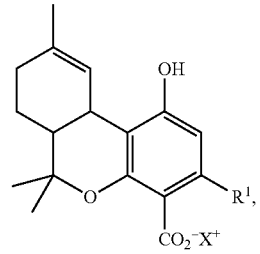

(3)

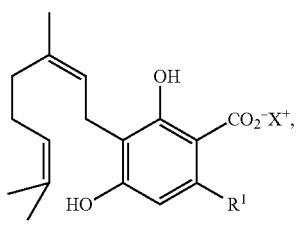
(4)

and stereoisomers thereof,
wherein $R^1$ is a straight-chain, branched, or cyclic hydrocarbon residue comprising up to 12 C atoms, and
$X^+$ is selected from the group consisting of $NH_4^+$; mono-, di- or trivalent metal ions, primary, secondary, tertiary, or quaternary organic ammonium ions comprising up to 48 C atoms; hydrazinium ion ($N_2H_5^+$) or organic derivatives thereof; hydroxylammonium ion ($NH_3OH^+$) or organic derivatives thereof; guanidinium ion ($CN_3H_6^+$) or organic derivatives thereof; N,N-dicyclohexylamine-$H^+$, N,N-dicyclohexyl-N-ethylamine-$H^+$; and an hydrogenium cation of a pharmaceutical active substance comprising at least one basic nitrogen atom.

2. The compound as claimed in claim 1, and/or the stereoisomers thereof, wherein the compound and/or the stereoisomers thereof are in crystalline form, in amorphous form, or are in solution.

3. A process for the production of a compound chosen from formulae (1)-(4)

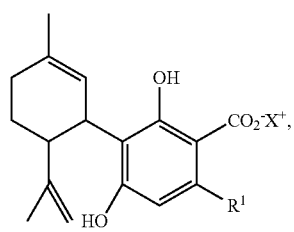
(1)

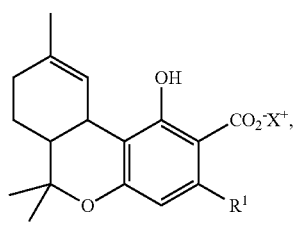
(2)

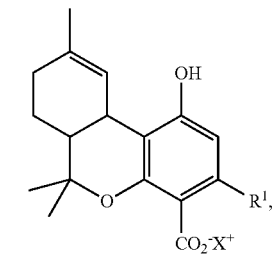
(3)

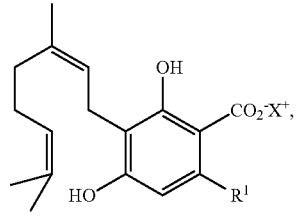
(4)

and stereoisomers thereof,
wherein $R^1$ is a straight-chain, branched, or cyclic hydrocarbon residue comprising up to 12 C atoms, and
$X^+$ is selected from the group consisting of $H^+$; $NH_4^+$; mono-, di- or trivalent metal ions; primary, secondary, tertiary, or quaternary organic ammonium ions comprising up to 48 C atoms; hydrazinium ion ($N_2H_5^+$) or organic derivatives thereof; hydroxylammonium ion ($NH_3OH^+$) or organic derivatives thereof; guanidinium ion ($CN_3H_6^+$) or organic derivatives thereof; N,N-dicyclohexylamine-$H^+$; N,N-dicyclohexyl-N-ethylamine-$H^+$; and an hydrogenium cation of a pharmaceutical active substance comprising at least one basic nitrogen atom,
comprising
a) isolating cannabinoid carboxylic acid by a method selected from the group consisting of: producing synthetic cannabinoid carboxylic acids in a chemical reaction, and extracting natural cannabinoid carboxylic acids from plant material or cell cultures of *Cannabis sativa*, and
b) treating the synthetic cannabinoid carboxylic acids, or the extracts of the natural cannabinoid carboxylic acids with a suitable inorganic base, a suitable organic base, a suitable inorganic and/or a suitable organic salt, in a suitable solvent, thereby precipitating out poorly soluble salts of the cannabinoid carboxylic acids; and
wherein the compound and/or the stereoisomers thereof are in crystalline form, in amorphous form, or are in solution.

4. The process as claimed in claim 3, wherein the chemical reaction is a carboxylation of natural or synthetic neutral cannabinoids.

5. The process as claimed in claim 3, wherein the chemical reaction is an acid-catalyzed terpenylation of unprotected or protected alkylresorcylic ester of formula (5),

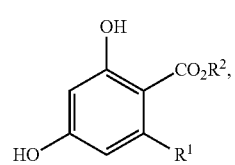
(5)

and subsequent saponification, wherein $R^1$ is a straight-chain, branched, or cyclic hydrocarbon residue comprising up to 12 C atoms, and $R^2$ is H or a straight-chain or branched alkyl comprising up to 16 C atoms, optionally substituted with phenyl, hydroxy, methoxy, ethoxy, halogen, or nitrile.

6. The process as claimed in claim 3, wherein the extraction of the natural cannabinoid carboxylic acid comprises drying the plant materials and contacting the plant materials or cell culture of *Cannabis sativa* with a suitable solvent selected from the group consisting of: hydro-carbons comprising up to 30 C atoms; petroleum distillates chosen from petroleum ether, ligroin, kerosene, naphtha, and halogenated hydrocarbons comprising up to 12 C atoms; carbon disulfide; esters and ethers with up to 16 C atoms; alcohols, ketones and nitriles comprising at least 4 and up to 12 C atoms; water comprising basic additives; water comprising detergents; lower alcohols comprising up to 4 C atoms; acetonitrile; propionitrile; acetone; carbon dioxide; and liquefied sulfur dioxide; and any combination(s) thereof; thereby obtaining an extract of cannabinoid carboxylic acid stored on the outside of cells; concentrating the extract of cannabinoid carboxylic acid in a countercurrent process; and evaporating the extract at temperatures below 60° C.

7. The process as claimed in claim 6, wherein cannabinoid carboxylic acid salts are produced with a solvent selected from the group consisting of water, alcohols, esters, ethers, ketones, hydrocarbons, halogenated hydrocarbons, and nitriles comprising up to 20 C atoms.

8. The process as claimed in claim 3, wherein the inorganic or organic bases are selected from the group consisting of primary, secondary and tertiary organic amines comprising up to 48 C atoms.

9. The process as claimed in claim 8, wherein the inorganic base is complexed in order to increase the solubility.

10. The process as claimed in claim 3, wherein the organic salt is selected from the group consisting of primary, secondary, tertiary and quaternary organic ammonium salts.

11. The process as claimed in claim 10, wherein the salts obtained are recrystallized from a lower alcohol, ketone, nitrile, ester or ether with up to 8 carbon atoms.

12. The process for the production of pure cannabinoid acids from the compound and/or the stereoisomers thereof as claimed in claim 3 by addition of suitable water-soluble acids in a suitable solvent with a $pK_a$ below 7 and carbonic acid.

13. The process for the production of pure cannabinoids from the compound and/or the stereoisomers thereof as claimed in claim 3, wherein the compound and/or the stereoisomers thereof are thermally decomposed.

14. The process as claimed in claim 13, wherein the cannabinoid carboxylic acids or the salts thereof are contacted with catalytic substances to accelerate the decarboxylation.

15. A composition comprising a mixture of compounds of formulae (1)-(4) as recited in claim 1, or stereoisomers thereof.

16. A compound chosen from formulae (1)-(4)

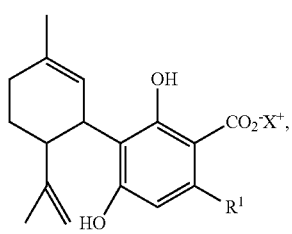
(1)

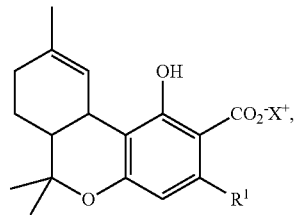
(2)

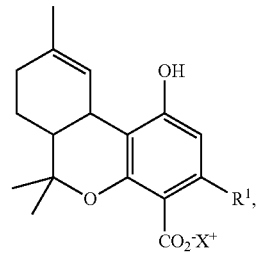
(3)

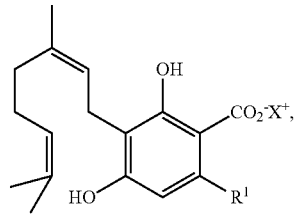
(4)

or the stereoisomers thereof,
wherein $R^1$ is a straight-chain, branched, or cyclic hydrocarbon residue comprising up to 12 C atoms, and
wherein X+ is an hydrogenium cation of a pharmaceutical active substance with at least one basic nitrogen atom.

17. The compound or the stereoisomers thereof of claim 16, wherein the pharmaceutical active substance is morphine, hydromorphone, methadone, or an isomer of methadone.

18. The process as claimed in claim 8, wherein the primary, secondary or the tertiary amine has one or more functional groups chosen from dicyclohexylamine, ammonia, hydrazine, hydroxylamine, guanidine, organic derivatives of hydrazine, organic derivatives of hydroxylamine, and organic derivatives of guanidine.

19. The process of claim 18, wherein the organic derivatives of hydrazine, the organic derivatives of hydroxylamine, and/or the organic derivatives of guanidine oxides have one or more functional groups chosen from alkoxides, hydroxides, carbonates, hydrogen carbonates, carboxylates, tin, lead, bismuth, silver, and ammonia, and any combination(s) thereof.

20. The process as claimed in claim 10, wherein the organic ammonium salts comprises 48 C atoms.

21. The process as claimed in claim 20, wherein the ammonium salts further comprise functional groups chosen from organic derivatives of hydrazinium salts, hydroxylammonium salts and guanidinium salts.

22. The process as claimed in claim 14, wherein the catalytic substance is selected from surface-active transition metals and solutions of transition metals.

23. The process as claimed in claim 22, wherein the catalytic substance is iron-[III] chloride or silver nitrate.

24. The compound as claimed in claim 2, and/or the stereoisomers thereof, wherein the compound and/or the stereoisomers thereof are in crystalline form.

25. The compound as claimed in claim 2, and/or the stereoisomers thereof, wherein the compound and/or the stereoisomers thereof are in amorphous form.

26. The compound as claimed in claim 2, and/or the stereoisomers thereof, wherein the compound and/or the stereoisomers thereof are in solution.

27. The compound as claimed in claim 1, and/or the stereoisomers thereof, wherein $X^+$ is selected from the group consisting of $NH_4^+$; primary, secondary, tertiary, or quaternary organic ammonium ions comprising up to 48 C atoms; hydrazinium ion ($N_2H_5^+$) or organic derivatives thereof; hydroxylammonium ion ($NH_3OH^+$) or organic derivatives thereof; guanidinium ion ($CN_3H_6^+$) or organic derivatives thereof; N,N-dicyclohexylamine-$H^+$; N,N-dicyclohexyl-N-ethylamine-$H^+$; and an hydrogenium cation of a pharmaceutical active substance comprising at least one basic nitrogen atom.

28. The compound as claimed in claim 1, and/or the stereoisomers thereof, wherein $X^+$ is a monovalent metal ion.

29. The compound as claimed in claim 1, and/or the stereoisomers thereof, wherein $X^+$ is a divalent metal ion.

30. The compound as claimed in claim 1, and/or the stereoisomers thereof, wherein $X^+$ is a trivalent metal ion.

* * * * *